(12) United States Patent
De Fraine

(10) Patent No.: US 6,169,101 B1
(45) Date of Patent: *Jan. 2, 2001

(54) PYRIDINE DERIVATIVES AS FUNGICIDES

(75) Inventor: Paul John De Fraine, Wokingham (GB)

(73) Assignee: Zeneca Limited(GB)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/091,549

(22) PCT Filed: Jan. 16, 1997

(86) PCT No.: PCT/GB97/00117

§ 371 Date: Jun. 18, 1998

§ 102(e) Date: Jun. 18, 1998

(87) PCT Pub. No.: WO97/29088

PCT Pub. Date: Aug. 14, 1997

(30) Foreign Application Priority Data

Feb. 9, 1996 (GB) .................................................. 9602623

(51) Int. Cl.$^7$ ........................... A01N 43/40; C07D 213/64
(52) U.S. Cl. ........................... 514/345; 514/351; 546/300; 546/302
(58) Field of Search .................................. 546/300, 302; 514/345, 351

(56) References Cited

U.S. PATENT DOCUMENTS 5,021,581 * 6/1991 Clough et al. ........................ 546/309
5,089,510 * 2/1992 Tapolczay et al. ................... 514/345
5,157,037 * 10/1992 Schuetz et al. ....................... 514/269
5,166,216 11/1992 Schuetz et al. ....................... 514/406
5,185,342 * 2/1993 Hayase et al. ........................ 514/274
5,468,717 * 11/1995 Wenderoth et al. .................. 504/130

FOREIGN PATENT DOCUMENTS 0 278 595    8/1988   (EP) .
0 373 775   11/1989   (EP) .
0 350 691    1/1990   (EP) .
0 363 818    4/1990   (EP) .
0 398 692   11/1990   (EP) .
0 547 825 A2 12/1992  (EP) .
0 617 011 A2  4/1994  (EP) .

OTHER PUBLICATIONS

Cram and Hammond, "Organic Chemistry" 2nd ed. NY: McGraw–Hill Book C., 1964, pp. 565–567.

* cited by examiner

*Primary Examiner*—Patricia L. Morris
(74) *Attorney, Agent, or Firm*—Thomas R. Savitsky

(57) ABSTRACT

A fungicidal compound having general formula (I)

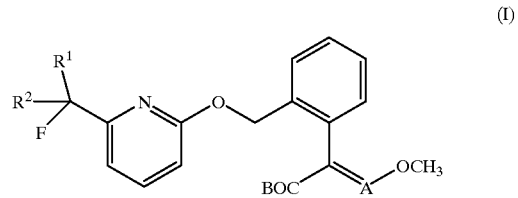

(I)

or a stereoisomer thereof, wherein A is CH or N, B is $OCH_3$ or $NHCH_3$, $R^1$ is H, chloro or methyl and $R^2$ is H, fluoro, chloro or methyl.

11 Claims, No Drawings

PYRIDINE DERIVATIVES AS FUNGICIDES

The present invention relates to novel nitrogen-containing heterocyclic compounds, to processes for preparing them, to compositions containing them and to methods of using them to combat fungi, especially fungal infections of plants.

More particularly, the invention relates to fungicidal compounds in which a substituted pyridine ring is attached through an oxymethylene linking group to a phenyl ring containing an ortho methyl β-methoxyacrylate group or methyl β-methoxyiminoacetate group or an amide derivative thereof.

Fungicidal compounds in which a substituted pyridine ring is linked through an oxymethylene group to a phenyl ring containing an ortho methyl β-methoxyacrylate group are described in, for example, EP-A-0278595 and EP-A-0350691. Such compounds include those in which the pyridine carries a 6-trifluoromethyl substituent. Similar compounds containing a methyl β-methoxyiminoacetate group and amide derivatives are described in, for example, EP-A-0363818 and EP-A-0398692. The compounds of the present invention show an unexpected advantage over the known compounds in respect of certain fungicidal properties.

According to the present invention there is provided a compound having the general formula (I):

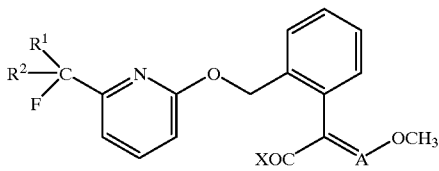

(I)

or a stereoisomer thereof, wherein A is CH or N, X is $OCH_3$ or $NHCH_3$, $R^1$ is H, chloro or methyl and $R^2$ is H, fluoro, chloro or methyl.

Of particular interest are compounds where A is N and X is $OCH_3$ or $NHCH_3$ and more particularly where A is CH and X is $OCH_3$.

Because the carbon-carbon double bond of the group $XOC.C=A.OCH_3$ is unsymmetrically substituted, the compounds of the invention may be obtained in the form of mixtures of (E)- and (Z)-geometric isomers. However, these mixtures can be separated into individual isomers, and this invention embraces such isomers and mixtures thereof in all proportions. The (E)-isomers with respect to the group $XOC.C=A.OCH_3$ are usually the more fungicidally active and form a preferred embodiment of the invention.

Further, when $R^1$ is not the same as $R^2$ and $R^2$ is not fluoro, the compounds of the invention may exist in the form of mixtures of optical isomers. However, these mixtures can be separated into the component isomers by known methods and this invention embraces such isomers and mixtures thereof in all proportions.

In one aspect the invention includes a compound of formula (I) or a stereoisomer thereof, wherein A is CH or N, X is $OCH_3$ or $NHCH_3$, $R^1$ is H, chloro or methyl and $R^2$ is fluoro or methyl. Suitably, A is N and X is $OCH_3$ or $NHCH_3$. Preferably A is CH and B is $OCH_3$.

In another aspect the invention includes a compound having the general formula (I) or a stereoisomer thereof, wherein A is CH or N, X is $OCH_3$ or $NHCH_3$, R1 is H or methyl and $R^2$ is fluoro or methyl. Suitably, A is N and X is $OCH_3$ or $NHCH_3$. Preferably A is CH and X is $OCH_3$.

In yet another aspect the invention includes a compound having the general formula (I) or a stereoisomer thereof, wherein A is CH or N and X is $OCH_3$ or $NHCH_3$, $R^1$ is H or chloro and $R^2$ is fluoro or methyl. Suitably, A is N and X is $OCH_3$ or $NHCH_3$. Preferably A is CH and X is $OCH_3$.

The present invention is illustrated by compounds of the general formula (II) listed in Tables 1 to 4. Throughout the Tables the W group has the (E)-configuration.

In the compounds of Table 1, W is $CH_3O.CH=C.CO_2CH_3$.

TABLE 1

(II)

| Compound No | $R^1$ | $R^2$ | Compound No | $R^1$ | $R^2$ |
|---|---|---|---|---|---|
| 1 | H | H | 6 | Cl | Cl |
| 2 | H | F | 7 | Cl | $CH_3$ |
| 3 | H | Cl | 8 | $CH_3$ | F |
| 4 | H | $CH_3$ | 9 | $CH_3$ | $CH_3$ |
| 5 | Cl | F | | | |

Table 2

Table 2 comprises 9 compounds having the same structural formulae and the same values of $R^1$ and $R^2$ as the correspondingly numbered compounds in Table 1, but in this case W is $CH_3O.CH=C.CONHCH_3$.

Table 3

Table 3 comprises 9 compounds having the same structural formulae and the same values of $R^1$ and $R^2$ as the correspondingly numbered compound in Table 1, but in this case W is $CH_3O.N=CO_2CH_3$.

Table 4

Table 4 comprises 9 compounds having the same structural formulae and the same values of $R^1$ and $R^2$ as the correspondingly numbered compound in Table 1, but in this case W is $CH_3O.N=C.CONHCH_3$.

Table 5

Table 5 shows melting points where measurable or selected proton NMR data obtained at 270 MHz for certain compounds described in Tables 1 to 4. Chemical shifts are measured at 20° C. in ppm from tetramethylsilane and deuterochloroform was used as solvent, unless otherwise stated. The following abbreviations are used:

| Compound No. (Table No.) | Melting Point ° C. | Proton NMR Data (δ) ppm |
|---|---|---|
| 2(1) | Oil | 3.64(3H, s); 3.81(3H, s); 5.29(2H, s); 6.28, 6.49, 6.70(1H, t); 7.1–7.4(4H, m); 7.55(1H, s); 7.56(1H, m); 7.67(1H, t). |

-continued

| Compound No. (Table No.) | Melting Point °C. | Proton NMR Data (δ) ppm |
|---|---|---|
| 2(3) | Oil | 3.86(3H, s); 4.03(3H, s); 5.28(2H, s); 6.37, 6.47, 6.68(1H, t); 6.80(1H, d); 7.2–7.6(4H, m); 7.68(1H, t); 7.70(1H, d). |
| 2(4) | 68–70 | 2.91(3H, d); 3.93(3H, s); 5.28(2H, s); 6.29, 6.49, 6.70(1H, t); 6.75(1H, brs); 6.80(1H, d); 7.19(1H, d); 7.2–7.6(4H, m); 7.68(1H, t). |
| 4(1) | Oil | [1.60(d), 1.68(d) - 3H]; 3.68(3H, s); 3.81(3H, s); 5.25(2H, s); [5.45(q), 5.45(q)-1H]; 6.65(1H, d); 7.01(1H, d); 7.1–7.6(5H, m); 7.57(1H, s). |
| 5(1) | Oil | 3.68(3H, s); 3.82(3H, s); 5.33(2H, s); 6.84(1H, d); 7.1–7.7(6H, m); 7.56(1H, s). |
| 8(1) | Oil | 1.94(3H, t); 3.67(3H, s); 3.78(3H, s); 5.30(2H, s); 6.78(1H, d); 7.1–7.7(7H, m); 7.56(1H, s). |
| 9(1) | Oil | 1.58(3H, s); 1.68(3H, s); 3.68(3H, s); 3.80(3H, s); 5.25(2H, s); 6.61(1H, d); 7.1–7.6(6H, m); 7.57(1H, s). | s = singlet
d = doublet
t = triplet
q = quartet
m = multiplet
br = broad
ppm = parts per million The compounds of formula (I) may be prepared by methods well documented in the literature. Suitable methods are disclosed, for example, in EP-A-0278595 and EP-A-0350691, the contents of which are incorporated here by reference.

Thus, compounds of formula (I) may be prepared by reacting the metal salt of a pyridone of formula (III):

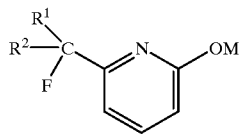

(III)

wherein $R^1$ and $R^2$ are as defined above and M is a metal atom, with a compound of formula (IV):

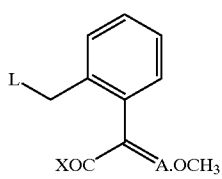

(IV)

wherein A and X are as defined above and L is a suitable leaving group.

In practice, a hydroxypyridine of formula (V):

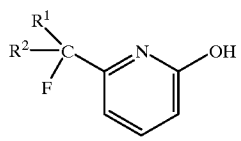

(V)

or the tautomeric pyridone is reacted with the compound (IV) in the presence of a suitable base such as silver carbonate in a suitable solvent such as toluene. In this case reaction proceeds via the compound III where M is silver. The leaving group L in the compound (IV) is suitably a halogen, (chloro, iodine or preferably bromine) or $OSO_2CF_3$. Typically, the reactants are refluxed in the toluene solvent for 3–4 hours.

Alternatively, the compounds of formula (I) may be prepared by reacting a pyridine of formula (VI):

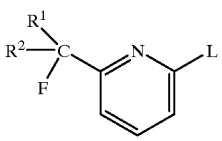

(VI)

wherein $R^1$, $R^2$ and L are as defined above, with the metal salt of a compound of formula (VII):

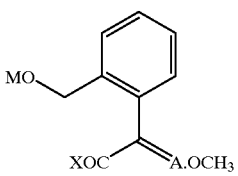

(VII)

wherein A, X and M are as defined above. Here the metal atom M is typically an alkali or alkaline earth metal, or it could be another metal such as silver.

Compounds of formula (IV), particularly where L is bromo, are well documented in the literature and can be prepared by the methods described therein; see for example EP-A-0203606 (where A is CH and X is $OCH_3$), EP-A-0363818 (where A is N and X is $OCH_3$) and EP-A-0398692 (where A is N and X is $NHCH_3$). The amides (where X is $NHCH_3$) may readily be prepared from the corresponding esters (where X is $OCH_3$) by treating the ester with methylamine in a suitable solvent such as methanol.

Compounds of formula (VII) can be prepared by forming the metal salt of the corresponding hydroxymethyl compound using conventional techniques. The hydroxymethyl compounds can be prepared, for example, by the methods described in WO 9307116.

The pyridines of formula (V) and (VI) are either commerically available or can be prepared from commerically available materials by methods described in the chemical literature. A novel method which is particularly convenient for preparing pyridines of formula (V) where $R^1$ is fluoro and $R^2$ is H or chloro, and which may be adapted to prepare other pyridines (V) or the tautomeric pyridones, involves the route displayed in Scheme 1.

In Scheme 1, the pyridone tautomer (V.1) of the pyridine (V) where $R^1$ is fluoro and $R^2$ is chloro and the pyridone tautomer (V.2) of the pyridine (V) where $R^1$ is fluoro and $R^2$ is H can be prepared from acyclic starting materials and used to make the compounds (I) where $R^1$ is fluoro and $R^2$ is chloro (I.1) or where $R^1$ is fluoro and $R^2$ is H (I.2).

The compound (I.2) can be made either by reacting the pyridone (V.2) with methyl 2-[2-(bromomethyl)phenyl]-3-methoxypropenoate (Compound (IV) where A is CH, X is $OCH_3$ and L is Br) or by reduction of the compound (I.1) using, for example, zinc dust. The pyridones (V.1) and (V.2) are prepared by decarboxylating the corresponding 2-hydroxy-nicotinic acid (VIII.1) or (VIII.2) at an elevated temperature above 190° C., typically at 250° C. Alternatively, the pyridone (V.2) is prepared by reduction of the pyridone (V.1). The 2-hydroxy-nicotinic acids (VIII.1) and (VIII.2) can be prepared by the general method described by R W Lang and P F Wenk in *Helv.Chim.Acta.*, 1988, 71(3), 596–601, involving the acidification of the corresponding nicotinamide (IX.1) or (IX.2). Alternatively, the 2-hydroxynicotinic acid (VIII.2) can be prepared by reduction of the 2-hydroxynicotinic acid (VIII.1).

(XII), which is commercially available, with ethyl vinyl ether (XIII).

Alternatively, the compounds of formula (I) wherein $R^1$ and $R^2$ are as defined above, A is CH and X is $OCH_3$ can be prepared from a phenylacetate of formula (XIV) or a ketoester of formula (XV) by the steps shown in Scheme 2. Throughout Scheme 2 the terms $R^1$ and $R^2$ are as defined above, $R^3$ is hydrogen or a metal such as sodium or

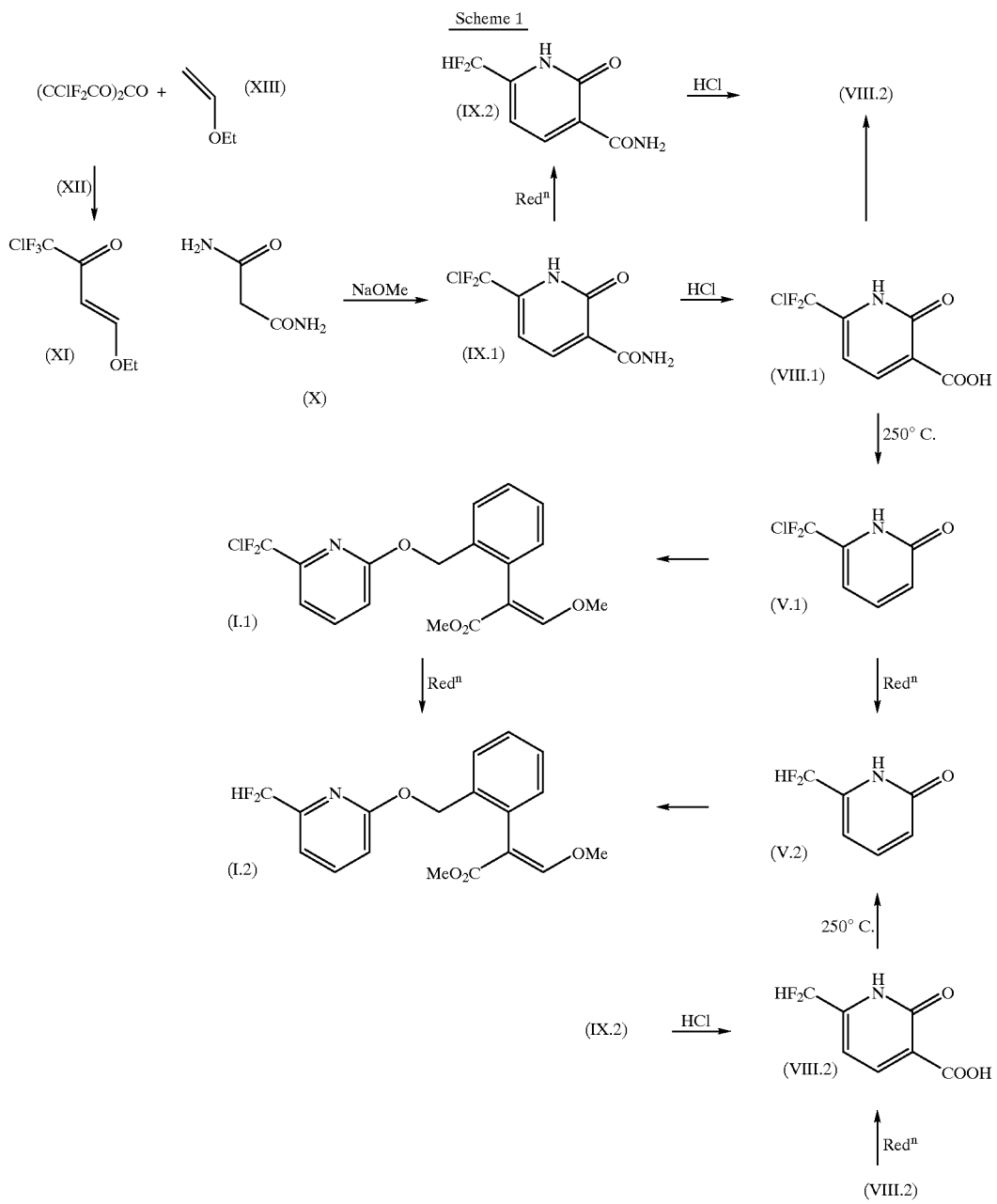

Scheme 1

The 2-hydroxynicotinamide (IX.1) can be prepared according to Lang & Wenk by cyclising a compound of formula (XI) with malonamide (X). The 2-hydroxynicotinamide (IX.2) can be prepared by reduction of the 2-hydroxynicotinamide (IX.1). The compound (XI) can be prepared by reacting chlorodifluoroacetic anhydride potassium and R is an alkyl group. Each transformation is performed at a suitable temperature and usually, though not always, in a suitable solvent.

Thus, a compound of formula (I) can be prepared by treatment of a phenylacetate of formula (XIV) with a base, such as sodium hydride or sodium methoxide, and methyl formate. If a species of formula $CH_3L^1$, wherein $L^1$ is a leaving group such as a halide (for example chloride, bromide or iodide), or a $CH_3SO_4$ anion, is then added to the reaction mixture, a compound of formula (I) is obtained. If a protic acid is added to the reaction mixture, a compound of formula (XVI), wherein $R^3$ is hydrogen, is obtained. Alternatively, the compound of formula (XVI) wherein $R^3$ is a metal such as sodium can be isolated from the reaction mixture.

A compound of formula (XVI) wherein $R^3$ is a metal can be converted into a compound of formula (I) by treatment with a species $CH_3L^1$, wherein L is as defined above. A compound of formula (XVI) wherein $R^1$ is hydrogen can be converted into a compound of formula (I) by successive treatment with a base, such as potassium carbonate, and a species of general formula $CH_3L^1$.

Alternatively, a compound of formula (I) can be prepared from an acetal of formula (XVII) by elimination of methanol under either acidic or basic conditions. Examples of reagents or reagent mixtures which can be used for this transformation are lithium diisopropylamide, potassium hydrogen sulphate (see, for example, T Yamada, H Hagiwara and H Uda, *J.Chem.Soc.Chemical Communications*, 1980, 838 and references therein, and triethylamine, often in the presence of a Lewis acid such as titanium tetrachloride (see, for example, K Nsunda and L Heresi, *J.Chem.Soc.Chemical Communications*, 1985, 1000).

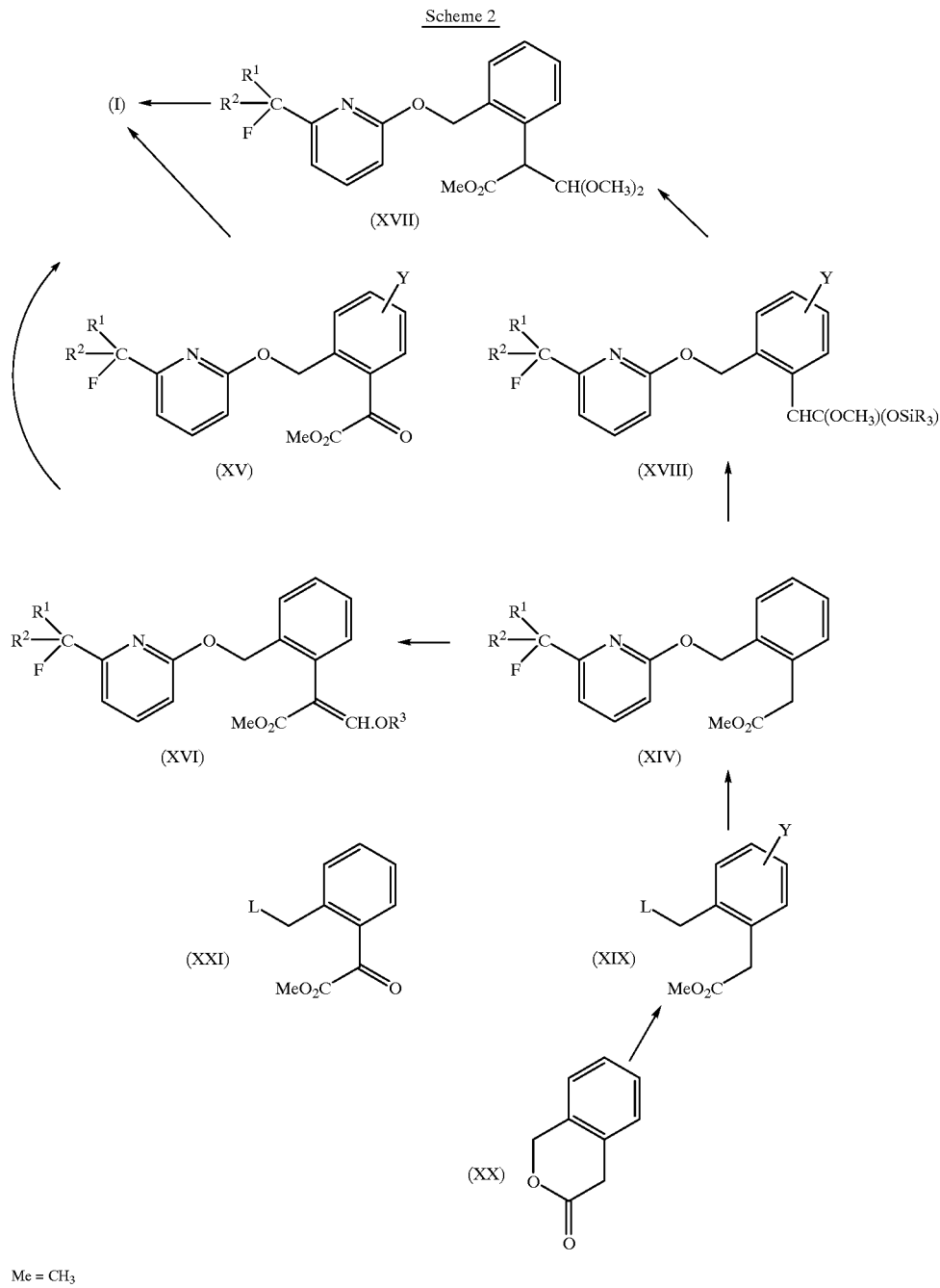

Scheme 2

Me = $CH_3$

Acetals of formula (XVII) can be prepared by treatment of a methyl silyl ketene acetal of formula (XVIII) with trimethyl orthoformate in the presence of a Lewis acid such as titanium tetrachloride (see, for example, K Saigo, M Osaki and T Mukaiyama, *Chemistry Letters*, 1976, 769).

A methyl silyl ketene acetal of formula (XVIII) can be prepared by treating a phenylacetate of formula (XIV) with a base and a trialkylsilyl halide of formula $R_3SiCl$ or $R_3SiBr$, such as trimethylsilyl chloride, or a base, such as triethylamine, and a trialkylsilyl triflate of formula $R_3Si$—$OSO_2CF_3$ (see, for example, C Ainsworth, F Chen and Y Kuo, *J.Organometallic Chemistry*, 1972, 46, 59).

It is not always necessary to isolate the intermediates (XVII) and (XVIII). Under appropriate conditions a compound of formula (I) can be prepared from a phenylacetate of formula (XIV) in "one pot" by the successive addition of suitable reagents listed above.

A phenylacetate of formula (XIV) can be prepared from a phenylacetate of formula (XIX). Thus, if a compound of formula (V) is treated with a suitable base such as silver carbonate and a phenyl acetate of formula (XIX) added, a phenylacetate of formula (XIV) is obtained.

A phenylacetate of formula (XIX) can be prepared by treating an isochromanone of formula (XX) with HL, wherein L is preferably bromine, in methanol. This transformation can also be accomplished in 2 steps if the isochromanone of formula (XX) is treated with HL in a non-alcoholic solvent, and the resulting phenylacetic acid is then esterified using standard procedures (see, for example, I Matsumoto and J Yoshizawa, Jpn. Kokai (Tokkyo Koho) 79138536,27.10.1979, *ChemAbs.*, 1980, 92, 180829h; and G M Lim, Y G Perron and R D Droghini, *Res.Discl.*, 1979, 188, 672, *Chem.Abs.*, 1980, 92, 128526t). Isochromanones of formula (XX) are well known in the chemical literature.

Alternatively, a compound of formula (I) can be prepared by treatment of a ketoester of formula (XV) with a methoxymethylenation reagent such as methoxymethylenetriphenyl-phosphorane (see, for example, EP-A-0044448).

A ketoester of formula (XV) can be prepared from a ketoester of formula (XXI), by treatment with a compound of formula (V) as described above. Ketoesters of formula (XXI) are described in EP-A-0331061.

Compounds of formula (I) where $R^1$ and $R^2$ are as defined above, A is N and B is $OCH_3$ may be prepared from ketoesters of formula (XV) by treatment with methoxylamine (or a salt of methoxylamine). Moreover these same compounds of formula (I) may be prepared by nitrosation of phenylacetates of formula (XIV) using nitrous acid or an ester of nitrous acid, in the presence of a base such as sodium methoxide, (see for example, O Touster, *Organic Reactions*, 1953, 7, 327 and S Kukolja et al, *J.Med.Chem.*, 1985, 28, 1896).

Compounds of formula (I) where A is N and X is the group $NHCH_3$, may be prepared by treating a compound of formula (I) where A is N and X is $OCH_3$ with methylamine in a suitable solvent such as methanol.

The compounds of formula (I) are active fungicides and may be used to control one or more of the following pathogens: *Pyricularia oryzae* on rice and wheat and other Pyricularia spp. on other hosts; *Puccinia recondita, Puccinia striiformis* and other rusts on wheat, *Puccinia hordei, Puccinia striiformis* and other rusts on barley, and rusts on other hosts e.g. turf, rye, coffee, pears, apples, peanuts, sugar beet, vegetables and ornamental plants; *Erysiphe graminis* (powdery mildew) on barley, wheat, rye and turf and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines; Cochliobolus spp., Helminthosporium spp., Drechslera spp. (Pyrenophora spp.), Rhynchosporium spp., Septoria spp. (including *Mycosphaerella graminicola* and *Leptosphaeria nodorum*), *Pseudocercosporella herpotrichoides* and *Gaeumannomyces graminis* on cereals (e.g. wheat, barley, rye), turf and other hosts; *Cercospora arachidicola* and *Cercosporidium personatum* on peanuts and other Cercospora species on other hosts, for example, sugar beet, bananas, soya beans and rice; *Botrytis cinerea* (grey mould) on tomatoes, strawberries, vegetables, vines and other hosts and other Botrytis spp. on other hosts; Alternaria spp. on vegetables (e.g. cucumber), oil-seed rape, apples, tomatoes, cereals (e.g. wheat) and other hosts; Venturia spp. (including *Venturia inaequalis* (scab)) on apples, pears, stone fruit, tree nuts and other hosts; Cladosporium spp. on a range of hosts including cereals (e.g. wheat); Monilinia spp. on stone fruit, tree nuts and other hosts; Didymella spp. on tomatoes, turf, wheat and other hosts; Phoma spp. on oil-seed rape, turf, rice, potatoes, wheat and other hosts; Aspergillus spp. and Aureobasidium spp. on wheat, lumber and other hosts; Ascochyta spp. on peas, wheat, barley and other hosts; *Plasmopara viticola* on vines; other downy mildews such as *Bremia lactucae* on lettuce, Peronospora spp. on soybeans, tobacco, onions and other hosts, *Pseudoperonospora humuli* on hops and *Pseudoperonospora cubensis* on cucurbits; Pythium spp. (including *Pythium ultimum*) on turf and other hosts; *Phytophthora infestans* on potatoes and tomatoes and other Phytophthora spp. on vegetables, strawberries, avocado, pepper, ornamentals, tobacco, cocoa and other hosts; *Thanatephorus cucumeris* on rice and turf and other Rhizoctonia species on various hosts such as wheat and barley, vegetables, cotton and turf; Sclerotinia spp. on turf, peanuts, oil-seed rape and other hosts; Sclerotium spp. on turf, peanuts and other hosts; Colletotrichum spp. on a range of hosts including turf, coffee and vegetables; *Laetisaria fuciformis* on turf; Mycosphaerella spp. on banana, peanut, citrus, pecan, papaya and other hosts; Diaporthe spp. on citrus, soybean, melon, pear, lupin and other hosts; Elsinoe spp. on citrus, vines, olives, pecans, roses and other hosts; Pyrenopeziza spp. on oil-seed rape and other hosts; *Oncobasidium theobromae* on cocoa causing vascular streak dieback; Fusarium spp., Typhula spp., *Microdochium nivale*, Ustilago spp., Urocystis spp., Tilletia spp., and *Claviceps purpurea* on a variety of hosts but particularly wheat, barley, turf and maize; Ramularia spp. on sugar beet and other hosts; post-harvest diseases particularly of fruit (e.g. *Pencillium digitatum* and *P. italicum* and *Trichoderma viride* on oranges, *Colletotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopezicula tracheiphila* and *Stereum hirsutum*; other pathogens on lumber, notably *Cephaloascus fragrans*, Ceratocystis spp., *Ophiostoma piceae*, Penicillium spp., *Trichoderma pseudokoningii, Trichoderma viride, Trichoderma harzianum, Aspergillus niger, Leptographium lindbergi* and *Aureobasidium pullulans*; and fungal vectors of viral diseases e.g. *Polymyxa graminis* on cereals as the vector of barley yellow mosaic virus (BYMV).

Further, some of the compounds may be useful as seed dressings against pathogens including Fusarium spp., Septoria spp., Tilletia spp., (e.g. bunt, a seed-borne disease of wheat), Ustilago spp. and Helminthosporium spp. on cereals, *Rhizoctonia solani* on cotton and *Pyricularia oryzae* on rice. In particular, some of the compounds show good eradicant activity against *Plasmopara viticola* and *Pythium ultimum*.

The compounds may move acropetally/locally in plant tissue. Moreover, the compounds may be volatile enough to be active in the vapour phase against fungi on the plant. The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor. It is preferred that all compositions, both solid and liquid formulations, comprise 0.0001 to 95%, more preferably 1 to 85%, for example 1 to 25% or 25 to 60%, of a compound as hereinbefore defined.

When applied to the foliage of plants, the compounds of the invention are applied at rates of 0.1 g to 10 kg, preferably 1 g to 8 kg, more preferably 10 g to 4 kg, of active ingredient (invention compound) per hectare.

When used as seed dressings, the compounds of the invention are used at rates of 0.0001 g (for example 0.00 g or 0.05 g) to 10 g, preferably 0.005 g to 8 g, more preferably 0.005 g to 4 g, of active ingredient (invention compound) per kilogram of seed.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods, or applied by land or aerial irrigation systems.

The term "plant" as used herein includes seedlings, bushes and trees. Furthermore, the fungicidal method of the invention includes preventative, protectant, prophylactic, systemic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or N,N-dimethylformamide). The compositions may also be in the form of water dispersible powders or water dispersible granules comprising wetting or dispersing agents to facilitate the dispersion in liquids. The powders and granules may also contain fillers and suspending agents.

The compositions may also be in the form of soluble powders or granules, or in the form of solutions in polar solvents.

Soluble powders may be prepared by mixing the active ingredient with a water-soluble salt such as sodium bicarbonate, sodium carbonate, magnesium sulphate or a polysaccharide, and a wetting or dispersing agent to improve water dispersibility/solubility. The mixture may then be ground to a fine powder. Similar compositions may also be granulated to form water-soluble granules. Solutions may be prepared by dissolving the active ingredient in polar solvents such as ketones, alcohols and glycol ethers. These solutions may contain surface active agents to improve water dilution and prevent crystallisation in a spray tank.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Aqueous suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the uptake, distribution, adhesive power and resistance to rain on treated surfaces, the different compositions can be better adapted for various utilities. Other additives may be included to improve the biological efficacy of the various formulations. Such additives can be surface active materials to improve the wetting and retention on surfaces treated with the formulation and also the uptake and mobility of the active material, or additionally can include oil based spray additives, for example, certain mineral oil and natural plant oil (such as soya bean and rape seed oil) additives, or blends of them with other adjuvants.

The invention compounds can be used as mixtures with fertilisers (e.g. nitrogen-, potassium- or phosphorus-containing fertilisers). Compositions comprising only granules of fertiliser incorporating, for example coated with, a compound of formula (I) are preferred. Such granules suitably contain up to 25% by weight of the compound. The invention therefore also provides a fertiliser composition comprising a fertiliser and the compound of general formula (I) or a salt or metal complex thereof.

Water dispersible powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and tri-isopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, alkyl glucosides, polysaccharides and the lecithins and the condensation products of the said partial esters with ethylene oxide. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use, these concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 1–85%, for example 1–25% or 25–60%, by weight of the active ingredient. After dilution to form aqueous preparations, such preparations may contain varying amounts of the active ingredient depending upon the intended purpose, but an aqueous preparation containing 0.0001 to 10%, for example 0.005 to 10%, by weight of active ingredient may be used.

The compositions of this invention may contain other compounds having biological activity, e.g. compounds having similar or complementary fungicidal activity or which possess plant growth regulating, herbicidal or insecticidal activity.

By including another fungicide, the resulting composition can have a broader spectrum of activity or a greater level of intrinsic activity than the compound of general formula (I) alone. Further the other fungicide can have a synergistic effect on the fungicidal activity of the compound of general formula (I). Examples of fungicidal compounds which may be included in the composition of the invention are (E)-N-methyl-2-(2-phenoxyphenyl)-2-methoxyiminoacetamide, (E)-N-methyl-2-[2-(2,5-dimethylphenoxymethyl)phenyl]-2-methoxyiminoacetamide, (RS)-1-aminopropylphosphonic acid, (RS)-4-(4-chlorophenyl)-2-phenyl-2-(1H-1,2,4-triazol-1-ylmethyl)butyronitrile, Z)-N-but-2-enyloxymethyl-2-chloro-2',6'-diethylacetanilide, 1-(2-cyano-2-methoxyiminoacetyl)-3-ethyl urea, 4-(2,2-difluoro-1,3-benzodioxol-4-yl)pyrrole-3-carbonitrile, 4-bromo-2-cyano-N,N-dimethyl-6-trifluoromethylbenzimidazole-1-sulphonamide, 5-ethyl-5,8-dihydro-8-oxo(1,3)-dioxol-(4,5-g)quinoline-7-carboxylic acid, α-[N-(3-chloro-2,6-xylyl)-2-methoxyacetamido]-γ-butyrolactone, N-(2-methoxy-5-pyridyl)-cyclopropane carboxamide, alanycarb, aldimorph, ampropylfos, anilazine, azaconazole, azafenidin, azoxystrobin, benalaxyl, benomyl, biloxazol, binapacryl, bitertanol, blasticidin S, bromuconazole, bupirimate, butenachlor, buthiobate, captafol, captan, carbendazim, carbendazim chlorhydrate, carboxin, carvone, chinomethionate, chlorbenzthiazone, chloroneb, chlorothalonil, chlorozolinate, clozylacon, copper containing compounds such as copper oxychloride, copper oxyquinolate, copper sulphate, copper tallate, and Bordeaux mixture, cycloheximide, cymoxanil, cyproconazole, cyprofuram, debacarb, di-2-pyridyl disulphide 1,1'-dioxide, dichlofluanid, dichlone, diclobutrazol, diclomezine, dicloran, didecyl dimethyl ammonium chloride, diethofencarb, difenoconazole, difenzoquat, diflumetorim, O,O-di-iso-propyl-S-benzyl thiophosphate, dimefluazole, dimetconazole, dimethon orph, dimethirimol, diniconazole, dinocap, dipyrithione, ditalimfos, dithianon, dodemorph, dodine, doguadine, edifenphos, epoxiconazole, etaconazole, ethirimol, ethoxyquin, ethyl (Z)-N-benzyl-N-([methyl (methylthioethylideneamino-oxycarbonyl)amino]thio)-β-alaninate, etridiazole, famoxadone, fenaminosulph, fenapanil, fenarimol, fenbuconazole, fenfuram, fenpiclonil, fenpropidin, fenpropimorph, fentin acetate, fentin hydroxide, ferbam, ferimzone, fluazinam, fludioxonil, fluoroimide, flumetover, fluquinconazole, flusilazole, flutolanil, flutriafol, folpet, fuberidazole, furalaxyl, furametpyr, furconazole-cis, guazatine, hexaconazole, hydroxyisoxazole, hymexazole, imazalil, imibenconazole, ipconazole, iprobenfos, iprodione, isopropanyl butyl carbamate, isoprothiolane, kasugamycin, kresoxim-methyl, mancozeb, maneb, mefenoxam, mepanipyrim, mepronil, metalaxyl, metconazole, methfuroxam, metiram, metiram-zinc, metsulfovax, myclobutanil, NTN0301, neoasozin, nickel dimethyldithiocarbamate, nitrothal-isopropyl, nuarimol, ofurace, organomercury compounds, oxadixyl, oxasulfuron, oxolinic acid, oxycarboxin, pefurazoate, penconazole, pencycuron, phenazin oxide, phosetyl-Al, phosphorus acids, phthalide, polyoxin D, polyram, probenazole, prochloraz, procymidone, propamocarb, propamocarb hydrochloride, propiconazole, propineb, propionic acid, prothiocarb, pyracarbolid, pyrazophos, pyrifenox, pyrimethanil, pyroquilon, pyroxyfur, pyrrolnitrin, quaternary ammonium compounds, quinconazole, quinomethionate, quinoxyfen, quintozene, rabenazole, sodium pentachlorophenate, spiroxamine, streptomycin, sulphur, tebuconazole, techlofthalam, tecnazene, tetraconazole, thiabendazole, thicyofen, thifluzamide, 2-(thiocyanomethylthio)benzothiazole, thiophanatemethyl, thiram, timibenconazole, tolclofos-methyl, tolylfluanid, triacetate salt of 1,1'-iminodi(octamethylene)diguanidine, triadimefon, triadimenol, triazbutyl, triazoxide, tricyclazole, tridemorph, triforine, triflumizole, triticonazole, validamycin A, vapam, vinclozolin, XRD-563, zineb and ziram. The compounds of general formula (I) can be mixed with soil, peat or other rooting media for the protection of plants against seed-borne, soil-borne or foliar fungal diseases.

The following Examples illustrate the invention. Throughout the Examples, the term 'ether' refers to diethyl ether, magnesium sulphate was used to dry solutions except where otherwise indicated, and solutions were concentrated under reduced pressure. All reactions were performed under an atmosphere of nitrogen and solvents were dried before use, where appropriate. Unless otherwise stated, chromatography was performed on a column of silica gel as the stationary phase. The following abbreviations are used throughout:

ppm = parts per million  DMF = N, N-dimethylformamide mp = melting point  THF = tetrahydrofuran Abbreviations for NMR data are as indicated in Table 5.

EXAMPLE 1

This Example illustrates the preparation of 6-difluoromethylpyrid-2-one.

6-Chlorodifluoromethyl-pyrid-2-one (0.3 g) was placed in a 3-necked flask and dissolved in acetic acid (20 ml). To this solution zinc (1.0 g of 325 mesh dust) was added and the flask lowered into an ultra-sonic bath. The reaction mixture was sonicated at room temperature for 90 minutes then filtered through 'Hyflo Supercel' which was washed through with ethyl acetate. The filtrate was concentrated and the residue diluted with water and neutralised with sodium bicarbonate and extracted with ethyl acetate. The combined extracts were dried and concentrated to give a solid which was washed with petrol and dried in air to give 6-difluoromethylpyrid-2-one (0.15 g, 67% yield) as a white solid m.p. 125–7° C.; $^1$H NMR (270 MHz): δ 6.31, 6.53, 6.75 (1H,t), 6.56(1H,m), 6.75(1H,m), 7.52(1H,m), 12.5(1H, brs) ppm.

6-Chlorodifluoromethyl-2-hydroxynicotinic acid (1.1 g) was heated to 250° C. for 10 minutes until the effervescence had ceased. On cooling it was taken up in ethyl acetate and the organic phase washed with saturated sodium bicarbonate solution. The combined organic phase was dried, decolourised with activated charcoal and concentrated to give 6-chlorodifluoromethylpyrid-2-one (0.41 g, 47% yield) as an off white solid; $^1$H NMR (270 MHz): δ 6.89(2H,m), 7.12(1H,t), 13.5(1H,brs) ppm.

6-Chlorodifluoromethyl-2-hydroxynicotinamide (48.5 g) was heated in dilute sulphuric acid (36 ml in 250 ml water) for 12 hours. The reaction was concentrated to about half the volume and cooled in ice. The precipitate was filtered, washed with water and air dried to give 6-chlorodifluoromethyl-2-hydroxynicotinic acid (48.1 g, 98% yield) as a pale brown solid mp.131–3° C.; $^1$H NMR (270 MHz): δ 7.36(1H,d), 8.33(1H,d) ppm.

Malonamide (27.5 g) was added to a solution of sodium methoxide in methanol [prepared from sodium (8.7 g) and methanol (300 ml)]. After 15 minutes, (E)-ethoxy-1,1,1-chlorodifluorobuten-2-one (50.2 g) was added and the reaction mixture heated to reflux for 2 hours. After cooling, the reaction mixture was concentrated, then diluted with water, acidified with concentrated hydrochloric acid and the precipitate filtered off. This was washed with water and dried to give 6-chlorodifluoromethyl-2-hydroxynicotinamide (48.8 g, 81% yield) as a white solid mp. 230–232° C.; $^1$H NMR (270 MHz): δ 7.29(1H,brm), 8.03(1H,brs), 8.38(2H,d), 13.6 (1H,brs) ppm.

Pyridine (24 g) was added to a solution of ethyl vinyl ether (22 g) in chloroform (75 ml) under nitrogen keeping the temperature below 10° C. Chlorodifluoroacetic anhydride (75 g) was added over 90 minutes keeping the temperature below 20° C. The reaction was stirred for 16 hours then quenched with water. The chloroform layer was washed with water, dried and concentrated to give (E)-ethoxy-1,1,1-chlorodifluorobuten-2-one (50.2 g, 91% yield) as an orange liquid; $^1$H NMR (270 mhz): δ 1.43(3H,t), 4.12(2H, q), 5.89(1H,d), 7.90(1H,d) ppm.

EXAMPLE 2

This Example illustrates the preparation of methyl 2-[2-(6-difluoromethylpyrid-2-yloxymethyl)phenyl]-3-methoxypropenoate (Compound No 2 of Table 1).

6-Difluoromethylpyrid-2-one (3.2 g)(prepared as described in Example 1 or as described below), methyl 2-[2-(bromomethyl)phenyl]-3-methoxypropenoate (6.3 g) and silver carbonate (3.64 g) were refluxed together in toluene (200 ml) for 4 hours. After cooling, the reaction mixture was filtered through 'Hyflo supercel' which was washed through with ethyl acetate. Concentration and chromatography using dichloromethane as the eluant gave the title compound (3.3 g, 42% yield) as a clear pale yellow oil; $^1$H NMR given in Table 5.

To a solution of 2-tert-butoxy-6-difluoromethylpyridine (4.3 g) in dichloromethane (25 ml) trifluoroacetic acid (2 ml) was added. The reaction was stirred for 16 hours and then concentrated. The residue was diluted with water and neutralised with sodium bicarbonate. The solid formed was extracted into ethyl acetate, dried and concentrated to give 6-difluoromethylpyrid-2-one (3.2 g, 72% yield) as a white solid; $^1$H NMR (270 MHz): δ 6.31, 6.53, 6.75 (1H,t), 6.56(1H,m), 6.75(1H,m), 7.52(1H,m), 12.5(1H,brs) ppm.

Diethylaminosulphur trifluoride (2.5 ml) was added to a solution of 2-tert-butoxy-6-pyridine carboxaldehyde (1.5 g) in dichloromethane (20 ml) at −40° C. The reaction was allowed to warm to room temperature then stirred for 2 hours before being quenched with water and extracted with dichloromethane. The organic extract was washed with brine, dried, concentrated and chromatographed using dichloromethane as the eluant to give 2-tert-butoxy-6-difluoromethylpyridine (1.1 g, 66% yield) as a pale brown oil, $^1$H NMR (270 MHz): δ 1.58(9H,s), 6.26, 6.48, 6.69(1H, t), 6.71(1H,d), 7.11(1H,d), 7.61(1H,t) ppm.

"Butyl lithium (13.6 ml of a 2.5M solution in hexane) was added to a solution of 2-bromo-6-tert-butylpyridine (4.0 g) in THF (100 ml) at −90° C. This was stirred for 30 minutes then DMF (3 ml) in THF (15 ml) was added quickly. The reaction was allowed to reach room temperature then quenched with a saturated solution of ammonium chloride and extracted with ether. The combined organic extract was washed with brine, dried and concentrated to give 2-tert-butoxy-6-pyridine carboxaldehyde (2.8 g, 93% yield ) as a brown liquid; $^1$H NMR (270 MHz): δ 1.65(9H,s), 6.89(1H, s), 7.51(1H,d), 7.68(1H,t), 9.92(1H,s) ppm.

2,6-Dibromopyridine (50 g) was added to a solution of potassium tert-butoxide (35.5 g) in tert-butanol (300 ml). The mixture was heated to reflux for 3.5 hours then cooled and concentrated. The residue was quenched with water and extracted into ethyl acetate. The combined organic extracts were washed with brine, dried and concentrated to give 2-bromo-6-tert-butylpyridine (21.4 g, 44% yield ) as a clear oil; $^1$H NMR (270 MHz): δ 1.55(9H,s), 6.58(1H,d), 6.98 (1H,d), 7.33(1H,t)ppm.

EXAMPLE 3

This Example illustrates the preparation of methyl 2-[2-(6-difluoromethylpyrid-2-yloxymethyl)phenyl]-(O-methyloximino)acetate. (Compound No 2 of Table 3).

6-Difluoromethylpyrid-2-one (1.45 g), 2-[2-(bromomethyl)phenyl]glyoxylate O-methyloxime (2.5 g) and silver carbonate (1.3 g) were refluxed together in toluene (200 ml) for 3 hours. A further portion of 6-difluoromethylpyrid-2-one (0.73 g), 2-[2-(bromomethyl) phenyl]glyoxylate O-methyloxime (1.1 g) and silver carbonate (0.6 g) was added and the mixture refluxed for a further 6 hours After cooling the reaction mixture was filtered through 'Hyflo supercel' which was washed through with ethyl acetate. Concentration and chromatography using dichloromethane as the eluant gave a yelow oil which was triturated with hexane and tert-butyl methyl ether to give the title compound (0.89, 24% yield) as a white solid; $^1$H NMR given in Table 5.

EXAMPLE 4

This Example illustrates the preparation of methyl 2-[2-(6-difluoromethylpyrid-2-yl-oxymethyl)phenyl]-(O-methyloximino)acetamide. (Compound No 2 of Table 4).

Methyl 2-[2-(6-difluoromethylpyrid-2-yloxymethyl) phenyl]-(O-methyloximino)-acetate (0.43 g, as prepared in Example 3) was dissolved in methylamine (20 ml of a 33% solution in ethanol) and stirred for 1 hour. The reaction mixture was concentrated and the volatiles removed in vacuo to give the title compound (0.41 g, 96% yield) as a pale brown oil; $^1$H NMR given in Table 5.

EXAMPLE 5

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. The formulations (100 ppm active ingredient) were sprayed on to the foliage or applied to the roots of the plants in the soil. The sprays were applied to maximum retention and the root drenches to a final concentration equivalent to approximately 40 ppm a.i. in dry soil. Tween 20 was added to give a final concentration of 0.05% when the sprays were applied to cereals.

For most of the tests the compounds were applied to the soil (roots) or to the foliage (by spraying) one or two days before the plant was inoculated with the disease. Exceptions were the tests on Erysiphe graminis and Puccinia recondita in which the plants were inoculated 24 hours and 48 hours, respectively, before treatment. Foliar pathogens were applied by spray as zoosporangial suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease level present (i.e. leaf area covered by actively sporulating disease) on each of the treated plants was recorded using the following assessment scale:

0 = 0% disease present

1 = 0.1-1% disease present

3 = 1.1-3% disease present

5 = 3.1-5% disease present

10 = 5.1-10% disease present

20 = 10.1-20% disease present

30 = 20.1-30% disease present

60 = 30.1-60% disease present

90 = 60.1-100% disease present

Each assessment was then expressed as a percentage of the level of disease present on the untreated control plants. This calculated value is referred to as a POCO (Percentage of Control) value. An example of a typical calculation is as follows:

Disease level on treated control = 90

Disease level on treated plant = 30

$$POCO = \frac{\text{disease level on treated plant}}{\text{disease level on untreated control}} \times 100 = \frac{30}{90} \times 100 = 33.3$$

This calculated POCO value is then rounded to the nearest of the values in the 9-point assessment scale shown above. In this particular example, the POCO value would be rounded to 30. If the calculated POCO falls exactly mid-way between two of the points, it is rounded to the lower of the two values.

The results are shown in Table 6.

TABLE 6

| Compound No (Table No) | ERYSGT | LEPTNO | PUCCRT | PLASVI | PHYTIN | VENTIN |
|---|---|---|---|---|---|---|
| 2(1) | 0 | 0 | 0 | 0 | 0 | 0 |
| 2(3) | 0 | 10 | — | 0 | 0 | 0 |
| 2(4) | 0 | 0 | — | 0 | 5 | 0 |
| 4 | 0 | 0 | 0 | 0 | — | 0 |
| 5 | 0 | 0 | 0 | 0 | 0 | 0 |
| 8 | 0 | 0 | 0 | 0 | 0 | 0 |
| 9 | 0 | 0 | 0 | 0 | 0 | 0 |

—No result

Unless stated otherwise, data represent activity following application as a combined foliar spray and root drench treatment at 100 ppm.

| Keys to Diseases | | | |
|---|---|---|---|
| ERYSGT | Erysiphe graminis tritici | PLASVI | Plasmopara viticola |
| LEPTNO | Septoria nodorum | PHYTIN | Phytophthora infestans lycopersici |
| PUCCRT | Puccinia recondita | | |
| | | VENTIN | Venturia inaequalis |

What is claimed is:

1. A compound having the formula (I):

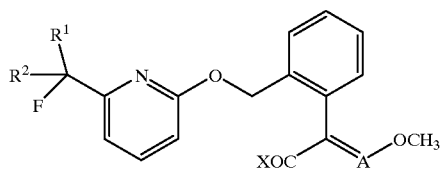

or a stereoisomer thereof, wherein A is CH or N, X is OCH$_3$ or NHCH$_3$, R$^1$ is H, chloro or methyl, and R$^2$ is H, fluoro, chloro or methyl.

2. A compound according to claim 1 wherein R$^1$ is H, chloro or methyl and R$^2$ is fluoro or methyl.

3. A compound according to claim 1 wherein R$^1$ is H or methyl and R$^2$ is fluoro or methyl.

4. A compound according to claim 1 wherein R$^1$ is H or chloro and R$^2$ is fluoro or methyl.

5. A compound according to claim 1 wherein A is CH and X is OCH$_3$.

6. A compound according to claim 1 which is in the form of the (E)-isomer with respect to the group XOC.C=A.OCH$_3$.

7. A process for preparing a compound according to claim 1 which comprises reacting the metal salt of a pyridone of formula (III):

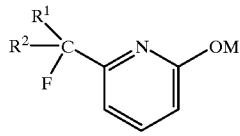

(III)

wherein R$^1$ and R$^2$ are as defined in claim 1 and M is a metal atom, with a compound of formula (IV):

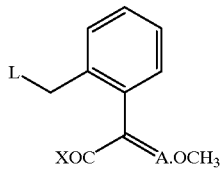

(IV)

wherein A and X are as defined in claim 1 and L is halogen or OSO$_2$CF$_3$, in a solvent.

8. A process for preparing a compound according to claim 1 which comprises reacting a pyridine of formula (VI):

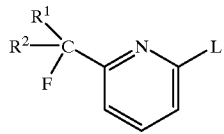

(VI)

wherein R$^1$ and R$^2$ are as defined in claim 1 and L is halogen or OSO$_2$CF$_3$, with the metal salt of a compound of formula (VII):

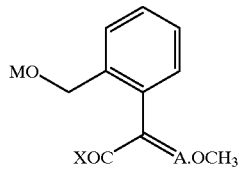

(VII)

wherein A and X are as defined in claim 1 and M is a metal atom, in a solvent.

9. A fungicidal composition comprising a fungicidally effective amount of a compound according to claim 1 and a fungicidally acceptable carrier or diluent therefor.

10. A method of combating fungi which comprises applying to plants, to the seeds of plants or to the locus of the plants or seeds, a fungicidally effective amount of a compound according to claim 1.

11. A method of combating fungi which comprises applying to plants, to the seeds of plants or to the locus of the plants or seeds, a fungicidally effective amount of a composition according to claim 3.

* * * * *